United States Patent [19]

Koermer

[11] Patent Number: 4,506,095
[45] Date of Patent: Mar. 19, 1985

[54] PRODUCTION OF LINEAR ALKENOIC ACIDS AND ESTERS

[75] Inventor: Gerald S. Koermer, Springfield, N.J.

[73] Assignee: Celanese Corporation, New York, N.Y.

[21] Appl. No.: 476,450

[22] Filed: Mar. 17, 1983

[51] Int. Cl.$^3$ .................... C07C 67/347; C07C 57/10
[52] U.S. Cl. .................... 560/205; 560/214; 562/601
[58] Field of Search ................ 560/205, 214; 562/601

[56] References Cited

U.S. PATENT DOCUMENTS

| | | | |
|---|---|---|---|
| 2,969,408 | 1/1961 | Nowlin et al. | 585/513 |
| 3,013,066 | 12/1961 | Alderson | 560/205 |
| 3,783,136 | 1/1974 | Inukai et al. | 560/205 |
| 4,085,275 | 4/1978 | Gambell et al. | 560/214 |

OTHER PUBLICATIONS

Matkovskii, P. E. et al., Chemical Abstracts, vol. 81, (1974), #78,514n.
Sumitomo Chemical Co., Ltd. Chemical Abstracts, #17146e, (1966), (French 1,424,091).
Krauch, Helmut et al., Organic Name Reactions, John Wiley & Sons, Publ., (1964), pp. 513-514.
Albisetti, C. J. et al., J. Am. Chem. Society, 89, (1956), pp. 2637-2641.

Primary Examiner—Natalie Trousof
Assistant Examiner—L. Hendriksen
Attorney, Agent, or Firm—Depaoli & O'Brien

[57] ABSTRACT

This invention provides a process for producing alkenoate products in the presence of an ethylaluminum dichloride type catalyst, such as the production of methyl 5-hexenoate by the reaction between propylene and methyl acrylate.

4 Claims, No Drawings

PRODUCTION OF LINEAR ALKENOIC ACIDS AND ESTERS

BACKGROUND OF THE INVENTION

Linear carboxylate derivatives find large volume application as components in detergent formulations, synthetic lubricants, and the like.

Another linear carboxylate compound of commercial importance is sorbic acid, which is sold as a preservative and antioxidant. The estimated United States market is 10-13 million pounds per year.

Sorbic acid is produced in one method by the reaction of ketene with crotonaldehyde. A disadvantage of the procedure is the formation of tar byproducts. Another synthesis method is disclosed in U.S. Pat. No. 4,158,741, which involves a catalytic conversion of γ-vinyl-γ-butyrolactone.

Various processes are known for dehydrogenation of saturated acid esters to alkenoic acid esters, such as that described in U.S. Pat. No. 3,652,654.

It is also known that unsaturated carboxylic acid esters can be produced by heating an olefin with an α,β-unsaturated carboxylic ester in the absence of a catalyst. The reaction is slow, and requires a high temperature over an extended reaction period. As reported in J.A.C.S., 78, 2637 (1956), only 13 percent methyl 5-hexenoate is obtained by heating a propylene and methyl acrylate mixture at 250° C. for nine hours. Heptene-1 and methyl acrylate provide a 35 percent yield of unsaturated carboxylate ester when heated at 230°-240° C. for 30-35 hours. Generally, an isomeric mixture of products is obtained.

U.S. Pat. No. 3,783,136 describes an improved process for conducting the reaction of an olefin with an acrylate compound to yield an alkenoate product, wherein the condensation is accomplished in the presence of an $AlCl_3$ or $AlBr_3$ catalyst. The use of this type of catalyst has the disadvantage that there is formation of a byproduct which is a hydrohalogenated derivative of the olefin reactant.

There remains a need for new and improved methods for synthesizing alkenoate derivatives, particularly of the linear type.

Accordingly, it is an object of this invention to provide an improved process for producing alkenoate esters and acids.

It is another object of this invention to provide a process for producing linear alkenoate esters by reaction of an alpha-olefin with an acrylate compound in the presence of an aluminum halide catalyst, with little or no yield of hydrohalogenated olefin byproduct.

It is a further object of this invention to provide a process for producing alkyl sorbate and sorbic acid.

Other objects and advantages of the present invention shall become apparent from the accompanying description and examples.

DESCRIPTION OF THE INVENTION

One or more objects of the present invention are accomplished by the provision of a process for producing linear alkenoate compounds which comprises reacting a linear 1-alkene with alkyl acrylate in the presence of an organometallic catalyst corresponding to the formula:

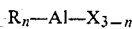

where R is an organic radical containing between about 1-12 carbon atoms, n is the integer 1 or 2, and X is chlorine or bromine.

Illustrative of linear 1-alkene reactants are alpha-olefins containing between about 3-18 carbon atoms such as propene, 1-butene, 1-pentene, 1-octene, 1-decene, 1-dodecene, and the like. Internal olefins and branched chain olefins may be employed if a non-linear alkenoate product is desired, e.g., an olefin such as 2-butene or cyclohexene.

Illustrative of alkyl acrylate reactants are esters in which the alkyl group contains between about 1-12 carbon atoms such as methyl acrylate, ethyl acrylate, isobutyl acrylate, heptyl acrylate, decyl acrylate, and the like. An alkyl-substituted acrylate such as methyl methacrylate may be employed if a non-linear alkenoate product is desired.

In the catalyst composition corresponding to the formula:

it is preferred that the organic radical R is attached by a carbon bond to the aluminum atom, for reasons detailed more fully hereinbelow. The R radical is preferably a hydrocarbyl substituent such as cyclohexyl or phenyl, and most preferably is an alkyl substituent containing between about 1-8 carbon atoms.

Illustrative of catalyst compositions are methylaluminum dichloride, dimethylaluminum chloride, ethylaluminum dibromide, diethylaluminum bromide, ethylaluminum dibromide, butylaluminum dichloride, decylaluminum dibromide, phenylaluminum dichloride, and the like.

The catalyst is employed in quantity between about 0.01-40 weight percent, preferably between about 10-30 weight percent, based on the weight of acrylate reactant.

The invention process can be conducted either in the absence or presence of a solvent. Normally, the reactants constitute the liquid reaction medium, particularly when the olefin reactant is employed in a molar excess such as between about 2-20 moles of olefin reactant per mole of acrylate reactant.

If a solvent is to be included in the reaction medium, it can be a conventional type such as hexane, xylene, carbon tetrachloride, ethylene chloride, ethyl acetate, tetrahydrofuran, and the like.

The reaction temperature can vary between about 25°-300° C., and usually will be in the range between about 25°-250° C.

The reaction pressure can vary between about 15-5000 psi, and preferably is in the range between about 15-2000 psi.

An important advantage of the present invention process is the use of a catalyst composition which prevents or suppresses the yield of undesirable hydrohalogenated byproduct, and thereby increases the selectivity and efficiency of the overall process. For example, when propylene is reacted with ethyl methacrylate in accordance with the invention process, the yield of 2-chloropropane is substantially eliminated:

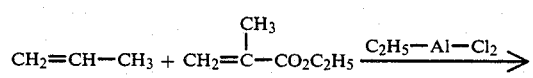

-continued

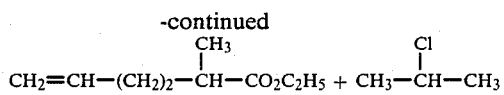

If AlCl₃ or AlBr₃ is employed as the catalyst in the above illustrated process, then a significant quantity of 2-chloropropane is obtained as a byproduct.

The 2-chloropropane byproduct appears to result from the reaction of propylene with hydrogen chloride. It is believed that the hydrogen chloride is generated by the reaction of AlCl₃ with water or some other proton source:

In contradistinction, a present invention catalyst interacts rapidly with hydrogen halide in the following manner:

The rapid removal of the hydrogen halide suppresses any subsequent reaction of the hydrogen halide with the olefin reactant to yield haloalkane byproduct in the invention process. The C—Al bond in the catalyst is readily susceptible under the process conditions.

An alternative method of removing the hydrogen halide is by neutralization of the hydrogen halide with a basic reagent. However, this prospective method is unsatisfactory in practice. A basic reagent tends to interfere with the reactivity of an aluminum halide catalyst. For example, if a basic reagent such as 1,8-bis(-dimethylamino)naphthalene (i.e., Proton Sponge ®) is employed with an aluminum chloride catalyst for the reaction of propylene with methyl acrylate, no methyl 5-hexenoate product is formed.

In another embodiment, the present invention contemplates the conversion of the alkenoate products to the corresponding alkadienoates by dehydrogenation. Catalysts and procedures for dehydrogenating alkenoates are disclosed in literature such as U.S. Pat. Nos. 3,652,654 and 4,085,275. Typical dehydrogenation catalysts include chromia alumina, calcium nickel phosphate, iron oxide, and the like.

In a further embodiment, hydrogenation of the alkenoate product over a hydrogenation catalyst (e.g., Group VIII metal) yields the corresponding saturated alkanoate, such as methyl 5-hexenoate to methyl hexanoate.

In a further embodiment, hydrolysis of the alkenoate product or the dehydrogenation or hydrogenation derivative thereof yields the corresponding free carboxylic product, such as sorbic acid or hexanoic acid.

The following Examples are further illustrative of the present invention. The catalysts and other specific ingredients and processing parameters are presented as being typical, and various modifications can be derived in view of the foregoing disclosure within the scope of the invention.

EXAMPLE I

This Example illustrates the production of methyl 5-hexenoate in accordance with the present invention process.

Into a 316 SS 300 ml stirred autoclave were placed 42 g (1.0 mole) propylene, 7.5 g (0.087 mole) methyl acrylate, 20 ml dry methylene chloride, 0.3 g hydroquinone and 1.40 g (0.011 mole) ethyl aluminum dichloride. The reaction mixture was stirred and heated to 149° C. for 18 hours. The maximum pressure observed was 780 psig.

After cooling, the excess propylene was slowly vented. Gas chromatographic analysis indicated 1.09 g methyl 5-hexenoate and 0.20 g 2-chloropropane. This corresponds to a 0.26% yield of 2-chloropropane from propylene and an 11% yield of methyl 5-hexenoate based on methyl acrylate.

The use of butene-1 in place of propylene provides the corresponding methyl 5-heptenoate product.

EXAMPLE II

This Example illustrates the production of methyl 5-hexenoate in accordance with the prior art.

Into a 316 stainless steel stirred autoclave were charged 36.1 g (0.86 mole) propylene, 5.5 g (0.64 mole) methyl acrylate, 20 ml dry methylene chloride, and 2.0 g aluminum chloride. The reactants were heated for 23 hours at 146° C. The maximum pressure observed was 575 psig. After cooling, excess propylene was very slowly vented.

Gas chromatographic analysis indicated 0.019 moles methyl 5-hexenoate (a 30% yield based on methyl acrylate) and 0.02 moles of 2-chloropropane (a 2.3% yield based on propylene).

The yield of undesirable byproduct 2-chloropropane in this Example was an order of magnitude greater than that obtained in Example I.

What is claimed is:

1. A process for producing alkyl 5-hexenoate which comprises reacting propylene with alkyl acrylate in an inert solvent medium containing ingredients consisting essentially of a polymerization inhibitor and an alkylaluminum dichloride catalyst, at a temperature between about 25°–250° C. and a pressure between about 15–2000 psi.

2. A process in accordance with claim 1 wherein the alkyl acrylate is methyl acrylate, and the product is methyl 5-hexenoate.

3. A process in accordance with claim 1 wherein the alkyl 5-hexenoate product is recovered, and dehydrogenated to alkyl sorbate.

4. A process in accordance with claim 3 wherein the alkyl sorbate is hydrolyzed to sorbic acid.

* * * * *